Figure 1:
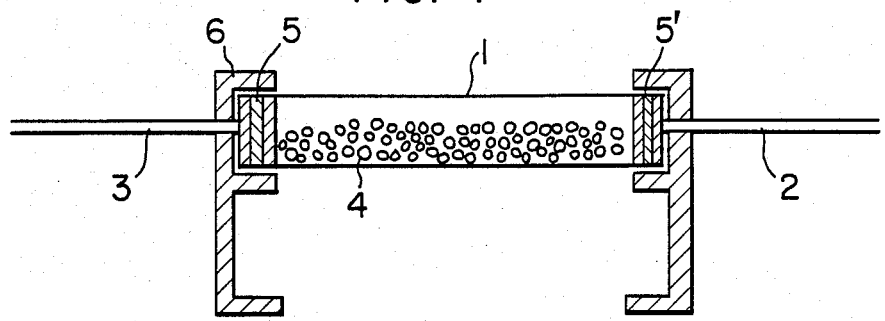

United States Patent [19]

Tanaka et al.

[11] Patent Number: 4,816,409
[45] Date of Patent: Mar. 28, 1989

[54] METHOD OF ELIMINATING TUMOR CELLS AND DEVICE THEREFOR

[75] Inventors: Toshihiko Tanaka, Arcadia, Calif.; Masayuki Nishida, Osaka, Japan

[73] Assignee: The Green Cross Corporation, Osaka, Japan

[21] Appl. No.: 582,446

[22] Filed: Feb. 22, 1984

[30] Foreign Application Priority Data

Feb. 23, 1983 [JP] Japan .................................. 58-30010

[51] Int. Cl.[4] .......................... B01J 8/02; B01D 27/00
[52] U.S. Cl. ..................................... 435/311; 210/638; 210/645; 210/927; 436/531; 436/541; 436/548; 436/824
[58] Field of Search .............................. 435/284–286, 435/288, 311; 436/548, 824, 531, 541; 210/927, 266, 280, 638, 645

[56] References Cited

U.S. PATENT DOCUMENTS

| 4,172,124 | 10/1979 | Koprowski et al. ................. 424/85 |
| 4,261,828 | 4/1981 | Brunner et al. ................. 435/288 X |
| 4,343,904 | 8/1982 | Birch et al. ..................... 435/285 X |
| 4,361,484 | 11/1982 | Larsson et al. ................. 435/269 X |
| 4,377,639 | 3/1983 | Lee ..................................... 435/285 |
| 4,409,105 | 10/1983 | Hayashi et al. ................. 210/927 X |
| 4,490,290 | 12/1984 | Gani et al. ....................... 210/927 X |
| 4,543,328 | 9/1985 | Keller et al. ..................... 435/29 X |
| 4,551,435 | 11/1985 | Liberti ................................ 436/541 |
| 4,693,985 | 9/1987 | Degen ............................... 436/531 |
| 4,714,556 | 12/1987 | Ambrus ............................. 210/638 |

OTHER PUBLICATIONS

Perry et al., Chemical Engineers' Handbook, 5th Ed., McGraw-Hill, N.Y., 1973, pp. 19-23.

Primary Examiner—Sidney Marantz
Attorney, Agent, or Firm—Cushman, Darby & Cushman

[57] ABSTRACT

Bone marrow or blood containing tumor cells can be freed from the tumor cells by bringing it into contact with an water-insoluble antitumor monoclonal antibody which is prepared according to the enzyme insolubilizing method and thereby combining the tumor cells with the insolublized antibody and destroying the tumor cells along with human serum complement on the insolublized antibody. The thus obtain bone marrow or blood free from tumor cells is used favorably in the autologous-bone-marrow transplantation method for treatment of tumor.

5 Claims, 1 Drawing Sheet

METHOD OF ELIMINATING TUMOR CELLS AND DEVICE THEREFOR

The invention relates to a filtration method and a filter for eliminating tumor cells or destroying and removing these from such a liquid as the bone marrow or blood of cancer patients.

In cases of bone marrow cancer such as leukemia or lymphoma and of solid cancer such as lung cancer, breast cancer, or malignant sarcoma, cancer cells circulate in the bone marrow or blood and thereby the cancer often metastasizes. Although bone marrow cancer such as leukemia or lymphoma can be cured by chemotherapy or radiotherapy to a remission state, the proliferation of remaining leukemia or lymphoma cells takes place again in most cases, so that the patient survival probability is extremely low. In case of the above solid cancer, a surgical operation to take out cancer tissues, chemotherapy, or radiotherapy is practiced. However, cancer cells remaining if any in the patient body will cause the recurrence and metastasis of the cancer. Thus, solid cancer also is a disease which the patients survive with very low probability as those of bone marrow cancer.

It is desirable that either bone marrow cancer cells or solid cancer cells in the patient body be killed completely by chemotherapy or radiotherapy, but strong chemotherapy or radiotherapy kills normal cells also, making difficult the restoration of health. Therefore autologous bone-marrow transplantation method has been attempted, which comprises, in case of bone marrow cancer, taking out bone marrow of the patient in a remission stage, storing it in a so-called incubator, killing the cancer cells together with parts of normal cells in the body by strong chemotherapy or radiotherapy during the storage of the bone marrw, and then inplanting the stored bone marrow of patient own to the body. According to this method, however, cancer cells remaining if any in the returned bone marrow will readily result in the recurrence of the cancer. This method leads to similar results in case of solid cancer, that is, when cancer cells remain in the living body, particularly in the bone marrow or blood, the cancer will readily recur and metastasize.

It is therefore necessary to eliminate tumor cells completely from the bone marrow or blood to be returned into the body.

The present inventors noticed the use of an antitumor monochlonal antibody (hereinafter, abbreviated as A.M. antibody) for the purpose of eliminating tumor cells or destroying and removing them from bone marrow or blood. However, the A.M. antibody is a protein derived from animals other than human beings, so that this protein of foreign animals is difficult to remove when mixed with human bone marrow or blood; a strong shock is often given when the bone marrow or blood contaminated with the foreign animal protein is returned into the patient body.

The object of this invention is to provide a method and a device for eliminating tumor cells or destroying and removing these from the substance, such as bone marrow, blood, or the like, to be administered into human bodies, without any hazards of contaminating the substance with the foreign protein.

According to the present invention, there is provided a method for eliminating tumor cells which comprises bringing bone marrow or blood containing tumor cells into contact with a water-insoluble antitumor monoclonal antibody to combine the tumor cells with the antibody and destroy the tumor cells along with human serum complement on the antibody, thereby eliminating the tumor cells, as well as a device therefor.

The device of this invention is one of filters that can be used as an incubator as well. The insolubilized A.M. antibody contained in the filter is shut off from the outlet by a filter plate having such pores as not to pass the insolubilized A.M. antibody, thereby preventing it from contaminating the filtrate. Preferably, the filter plate is such a one as having pore sizes of $40\mu$ and less in diameter, for example, Barrier-Filter (tradename, made by Johnson & Johnson Co.). Such a filter plate is used in a human blood extracorporeal circulating system for filtering off foreign substances e.g. bubbles, blood platelet coagula, erythrocyte coagula, fat granules, and fibrin agglomelates. In this way, it becomes possible to prevent not only the insolubilized A.M. antibody but also the above-mentioned foreign substances from the outflow. When using an incubator provided with a filter plate having pores that can prevent the insolubilized A.M. antibody only from the outflow, it is recommended for preventing other foreign substances from flowing into the patient body that the bone marrow or blood filtrate from the incubator be further passed through a suitable filter, e.g. the above-mentioned filter, before being returned into the body.

Particles of the water-insoluble A.M. antibody used in the filter of this invention have by themselves the ability to adsorb tumor cells, and destroy them in the presence of a human serum complement. The A.M. antibody is prepared by immunizing an animal to tumor cells, producing fused cell hybrids between the A.M. antibody producing cell and the marrow tumor cell of the animal, cloning these hybrids, and purifying the A.M. antibody obtained from some of these clones that produces the antitumor antibody which exhibits cytotoxicity to the present tumor cells. It is desirable to use the antibody highly purified to remove contaminating proteins except $\gamma$-globulin as far as possible. The water-insoluble A.M. antibody is obtained by subjecting the above purified A.M. antibody to the insolubilizing treatment known as a method for making enzymes insoluble in water.

Any purification method may be applied unless it denatures the $\gamma$-globulin fraction, to the preparation of the water-insoluble A.M. antibody for use in the filter or incubator of this invention. A preferred method of the purification is to take the fraction precipitated from an aqueous solution of the A.M. antibody by dissolving ammonium sulfate to a concentration of 40% in the solution.

For the insolubilization of the A.M. antibody, generally known methods for insolubilizing biologically active proteins such as enzymes are adaptable without losing the biological activity.

The hitherto practiced or proposed methods for insolubilizing enzymes include, for example, those of combining enzymes chemically with insoluble carriers (Japanese Patent Application Kokai No. 1838/71) such as combining an enzyme with a high molecular polysaccharide activated with cyanogen bromide or combining an enzyme with a silicon compound through covalent bonds, physical or electrostatic methods such as adsorption on active carbon (U.S. Pat. No. 2717852) or adsorption on a basic anion exchanger (Japanese Patent Application Kokai No. 6870/70), and methods of embeding an enzyme into a suitable matrix, e.g. a fibrin polymer (Japanese Patent Application Kokai No. 41584/74). The insolubilization of the A.M. antibody is accomplished by the same method as applied to the insolubilization of enzyme but using the purified A.M. antibody in place of the enzyme.

Favorable carriers for use in the insolubilization of the A.M. antibody by chemical combination therewith are water-insoluble organic or inorganic high molecular materials having groups, such as carboxyl groups or amino groups, which can combine with the A.M. antibody. Such high molecular materials include, for example, a polyacrylamide gel (tradename: Bio-gel P-300, supplied by Bio-Gel Co., U.S.A.), agarose (tradename: Sepharose 4B, supplied by Pharmacia Co., Sweden), dextrane (tradename: Sephadex G 200, DEAE-Sephadex, QAE-Sephadex, supplied by Pharmacia Co., Sweden), and materials derived from polysaccharides such as cellulose (DEAE-Cellulose, CM-Cellulose, AE-Cellulose, etc.), which do not directly combine with the A.M. antibody, by treating them with cyanogen bromide to give the combining ability. The method of treating polysaccharides with cyanogen bromide has been established as a method for separating proteins by a technique of affinity chromatography proposed by P. Cutrecasas and C.B. Anfinson [Method in Engymology, XXII, ed. by W.B. Jakoby, P 345 (1971)].

In the same way, groups combinable with the A.M. antibody can be given by a suitable agent, e.g. cyanogen bromide to macromolecular compounds, such as polyamide (e.g. nylon), polyacetal, polystyrene, etc., which have no such functional group. Moreover, even inorganic materials such as glass can be given amino groups, which are combinable with the A.M. antibody, by treating the materials with an aminoalkylsilane and thereby can be used for the insolubilization of the A.M. antibody.

Carriers used as physical or electrostatic adsorbents for fixing the A.M. antibody to insolubilize it include ion exchangers, e.g. DEAE-Sephadex and DEAE-Cellulose, besides diatomaceous earth and active carbon. Some bifunctional compounds, e.g. glutaraldehyde, can also be used as crosslinking agents for insolubilizing the A.M. antibody.

Gels or fibers of high molecular weight polymers are used as matrixes wherein an enzyme is embedded to be insolubilized. These gels or fibers also can be applied to the A.M. antibody by choosing proper means. For example, a monomer is polymerized in the presence of the A.M. antibody to imbed it in the formed polymer gel.

Treatments of the above-mentioned carriers for giving protein-combinable groups thereto are carried out under the following conditions:

(1) Polysaccharide carriers are treated usually with cyanogen bromide at pH 10–12 while cooling.

(2) Similarly, a methacrylate polymer having a macro-reticular structure is activated with cyanogen bromide at pH 10–12, giving good results.

(3) Glass, an inorganic carrier, is activated by reacting with an organosilane dissolved in an inert solvent, at room temperature for an adequate period of time.

(4) While all the carriers adsorbing the A.M. antibody can be used for insolubilizing it in so-called polymer-trap method, more simple carriers are preferable. For instance, the A.M. antibody is fixed in DEAE-Cellulose which has been thoroughly washed with water, by stirring at room temperature. This A.M. Antibody-bearing carrier can be further polymerized together with a secondary carrier.

Reactions of the A.M. antibody with the thus obtained carriers having the ability to combine with the A.M. antibody can be carried out at temperatures of about 3° to about 25° C. in the neutral state (pH 6–8).

It is desirable that the thus prepared insoluble A.M. antibody be in the form of numerous particles suitably used as the filtering bed and the particles be larger than the pore size of the filter plate and strong as far as possible. That is, the particles are desired to be larger than 40μ in diameter so as to be retained together with foreign substances in the filter and are desirably enough strong not to be disintegrated by bone marrow or blood. However, for the purpose of destroying tumor cells effectively, the particle sizes are preferred to be minimized under the limitation of being larger than 40μ. For the purpose of preventing the disintegration, the A.M. antibody insolubilized with a carrier can also be embedded further in a gel or fiber of high polymeric material.

As described above, the filter of this invention contains the insolubilized A.M. antibody, which is at least prevented by the filter plate from leakage to the filtrate outlet and is preferred to have an adequate surface area for effective capture and destruction of the tumor cells in bone marrow or blood. A mild stirring of the liquid, bone marrow or blood, in the filter is also possible as required for keeping the A.M. antibody in the suspension state.

The filter can be provided with a plurality of filter plates, thereby further ensuring the prevention of the insolubilized A.M. antibody from entering the patient body.

The filter of this invention may have in principle any form capable of sterile holding the insolubilized A.M. antibody, but preferably has a form applicable as an incubator. In this case, the treatment of the patient bone marrow or blood is carried out as follows: The bone marrow or blood is aseptically brought into contact with the insolubilized A.M. antibody in the incubator at about 37° C. for 60 minutes or more; then a human serum complement is added to the mixture and the reaction is continued at room temperture for 1–2 hours to destroy the tumor cells; thereafter the mixture is filtered through the filter plate and the filtered bone marrow or blood is returned into the patient body.

FIG. 1 shows a cross-sectional view of a typical example of the present filter which has a form applicable as the incubator. This filter has a room 1 containing the insolubilized A.M. antibody and two blocks of filter plates 5' and 5 each consisting of one or more layers of filter plates at the inlet 2 and the outlet 3. The filter plate blocks 5' and 5 serve to filter bone marrow or blood and the block 5 also serves to prevent the insolubilized A.M. antibody 4 from leaking to the outlet 3. The liquid introduced through the inlet 2 is mixed with the insolubilized A.M. antibody particles 4 in the room or chamber 1, the filter can be rotated by a driving motor 6 to keep the antibody in the suspension state.

Methods of various tests and assays relevant to this invention are described below. The values in Examples have been determined by these methods.

1. Assay for effect of eliminating-destroying tumor cells

The effect of eliminating-destroying tumor cells in bone marrow or blood can be determined by the following methods:

(1) Method using established tumor cell lines as indicator

In this method, established tumor cell lines are used as an indicator. This method is particularly applied to small-scale preliminary experiments for actual therapy to determine the amount ratio of the insolublized A.M. antibody to the bone marrow or blood in the filter serving also as an incubator (hereinafter, this type of filter is referred to as "filter-incubator").

One or more already established tumor cell lines are mixed with bone marrow or blood before the treatment in the filter-incubator of this invention. The mixing ratio may be $10^1$–$10^5$ cells of the established tumor cell lines to $10^6$ blood cells. The mixture is passed through the filter-incubator of this invention to destroy and eliminate the tumor cells. Then the treated bone marrow or blood is inoculated to a culture medium for established cell lines and cultivated. The grown colonies are analyzed in morphological and cytogenic aspects. On the other hand, the same monoclonal antibody as used to be insolubilized in the filter-incubator is added to the treated bone marrow or blood to react therewith, then an anti-mouse sheep immunoglobulin labelled with a fluorescent substance is added thereto, and the resulting mixture is analyzed with a fluorescence activated cell sorter.

In this way, it is confirmed that the present tumor cells have been destroyed and removed together with the established tumor cell lines by the treatment.

(2) Fluorescence activated cell sorter analysis

Lower density cells in the bone marrow or blood before the treatment in the filter-incubator of this invention are separated by velocity sedimentation method or density gradient centrifugal method and the resulting tumor-cell-containing fractions are concentrated to 20–250 times. The A.M. antibody is added to the concentrated tumor cell fraction and reacted at about 37° C. for about 60 minutes. After washing of the resulting mixture, an anti-mouse sheep immunoglobulin labelled with a fluorescent substance is added thereto and reacted at about 37° C. for about 60 minutes. After washing of the resulting mixture, the concentration of tumor cells is determined with a fluorescence activated cell sorter.

In the same manner, the concentration of tumor cells in the bone marrow or blood after treatment in the filter-incubator of this invention is determined to confirm that the tumor cells have been destroyed and eliminated by passing through the filter-incubator.

2. Tests for confirming the nontoxity to normal hematopoietic stem cells

When treating bone marrow in the filter-incubator of this invention, it is necessary in particular to confirm that hematopoietic stem cells are not destroyed or deactivated by this treatment. This confirmation test may be conducted simultaneously at the time the optimum amount ratio of the insolubilized A.M. antibody to the bone marrow or blood is determined before actual therapy by the preliminary small-scale experiment using the filter-incubator.

(1) Colony forming unit-granulocyte.monocyte (CFU-U)

For example, two bone marrow samples (each $2 \times 10^5$ cells) untreated and treated in the filter-incubator are inoculated respectively to media for CFU-C [W. A. Robinson and B. L. Pike, "Colony Growth of Human Bone Marrow Cells In Vitro", Symposium on Hematopoietic Cellular Differentiation (Ed. by F. Stohlman, New York, 1970)] and incubated at 37° C. for about 10 - about 14 days in an atmosphere of 7.5% $CO_2$ in air. Then, the granulacyte-macrophage colinies each containing 40 cells or more are enumerated under a dissecting microscope. In this way, it is confirmed that the treated sample is not different from the untreated in CFU-C.

(2) Colony forming unit-erythroid (CFU-E)

For example, two bone marrow samples (each $1 \times 10^6$ cells) untreated and treated in the filter-incubator are inoculated respectively to media for CFU-E (A. D. Tepperman, J. D. Curtis, and E. A. McCulloch, "Erythropoietic Colonies in Cultures of Human Marrow", Blood 1974, 44:659) and incubated at 37° C. for 7–9 days in an atmosphere of 7.5% $CO_2$ in air. Then, the erythroid colonies each composed of 8 cells or more are enumerated using an inverted microscope. The erythroid nature of the colonies are confirmed by benzidine staining. In this way, it is confirmed that the treated sample is not different from the untreated in CFU-E.

(3) Burst-forming unit-erythroid (BFU-E)

For example, two bone marrow samples (each $1 \times 10^6$ cells) untreated and treated in the filter-incubator are inoculated respectively to media for BFU-E (the paper shown in the preceding paragraph) and incubated at 37° C. for 14 days. Then, the colonies each composed of 50 cells or more are enumerated using an inverted microscope. In this way, it is confirmed that the treated sample is not different from the untreated in BFU-E.

(4) Colony forming unit-T-lynphocyte (CFU-TL)

For example, two bone marrow samples (each $4 \times 10^4$ cells) untreated and treated in the filter-incubator are inoculated respectively to media for CFU-TL (B. L. Pike and W. A. Robinson, "Human Bone Marrow Colony Growth in Agar-Gel", J. Cell Physiol., 76:77, 1970) and incubated at 36° C. for 7 days in an atmosphere of 5% $CO_2$ in air. Then, the colonies each composed of 30 cells or more are enumerated under a light microscope. In this way, it is confirmed that the treated sample is not different from the untreated in CFU-TL.

3. Optimum amount of insolubilized A.M. antibody

The optimum amount ratio of the insolubilized A.M. antibody to the bone marrow or blood to be treated is determined, for example, as follows:

A bone marrow or blood sample (3 ml) is treated in a 10-ml capacity filter-incubator of this invention (the capacity is 1/100 of that of the usual filter-incubator for adult purposes) which contains the insolubilized 0.25 ml of A.M. antibody (cytotoxity value: 1:100,000–1:1,000,000). The following items of analysis are made on the treated and untreated samples to determine the optimum amount.

a. Assay for effect of destroying and eliminating tumor cells
  ① Method using established tumor cell lines as indicator
  ② Fluorescence activated cell sorter analysis
b. Tests for confirming the nontoxity to normal hematopoietic stem cells ①  Colony forming unit-granulocyte.monocyte
②  Colony forming unit-erythroid
③  Burst-forming unit-erythroid
④  Colony forming unit-T-lymphocyte When any of the requirements in the above items is not fulfilled, the amount of the insolubilized A.M. antibody in the filter-incubator is varied to search for the proper condition.

Acutal therapy of larger scale is conducted under the optimum conditions determined by the above small-scale preliminary tests. The filter-incubators used in the actual therapy have capacities of 1000 ml for adults and of 500 ml for children.

EXAMPLE 1

About 200 ml of Sepharose 4B (supplied by Pharmacia Co., Sweden) of particle sizes 40–190 $\mu$ was activated by adding 50 g of cyanogen bromide with stirring, adjusting the pH at 11 with 4N NaOH while keeping the temperature at 10°–20° C., and continuing the stirring at pH 11 for about 10 minutes. The reaction mixture was filtered, the filter residue was washed with 0.1 M $NaHCO_3$, and about 200 ml of activated Sepharose 4B was obtained.

An anti-acute myeloid leukemia (AML) monoclonal antibody was obtained in the following manner: venous blood of an acute myeloid leukemia patient was taken aseptically in a test tube containing an anticoagulant heparin, and leukemia cells were isolated by means of Ficoll-Hypaque gradients. These leukemia cells were identified as AML cells by dyeing with lipase, Schiff's periodate, peroxidase, α-naphthylacetic acid esterase, and naphthol ASD chloroacetic acid esterase. The AML cells were stored in liquid nitrogen.

The AML ($15 \times 10^6$ cells) was intraperitoneally administered to a Balb/C mouse to immunize the mouse. After one week the ML ($15 \times 10^6$ cells) was intravenously administered as a booster to the mouse. Three days thereafter spleen cells of the mouse were taken out. Cell fusion was conducted by reacting these spleen cells ($3 \times 10^8$ cells) and myelom cells ($3 \times 10^7$ cells, P3/×63-Ag 8) of the mouse in a 43% polyethylene glycol solution at 37° C. for 1 minute and further in a 25% polyethylene glycol solution at 37° C. for 1 minute. This cell mixture was suspended in an RPMI medium, washed with an RPMI-HAT medium (hypoxanthine $10^{-4}$M, aminopterin $10^{-6}$M, thymidine $2 \times 10^{-5}$M), and suspended again in an RPMI medium. The cell suspension was placed in a flat-bottomed micro tissue culture plate having 96 wells so that $4 \times 10^5$ cells would be contained in each well. The cultivation was conducted in an HAT medium for the first week, in an HT medium (having the same composition as the HAT medium except containing no aminopterin) for the second and third weeks, and thereafter in an RPMI medium containing 15% bovine fetal serum to which glutamic acid and piruvic acid had been added. On 25th day after the cell fusion, the supernatants of the media in the wells were screened by a microcyte toxicity test [Am. J. Clin. Pathol., 69, 103–120 (1978)]. Fused cells, in one of the wells, showing specific cytotoxicity to AML cells are cloned by limiting dilution method. Fused cells of a specific clone alone are cultivated in a flask, and the culture was injected into the peritoneal cavity of a mouse to cultivate a high potency anti-AML monoclonal antibody in the ascites of the mouse. The grown anti-AML monoclonal (Lot TN 008) in ascites was purified in the following manner: To the ascites containing anti-AML monoclonal Lot TN 008, there was added an equal volume of 0.9% NaCl solution and then ammonium sulfate to a concentration of 40%. The precipitate formed was taken and dissolved by adding a 0.9% NaCl solution in twice the volume of the same solution first added. Further ammonium sulfate was added to a concentration of 40% and the precipitate fraction was taken and dissolved in a minimum amount of 0.9% NaCl solution. The resulting solution was dialyzed using a 0.02M phosphated buffered saline as outer liquid. After completion of the dialysis, the dialyzed solution was chromatographed through a DEAE-Cellulofine column.

Figure 2:
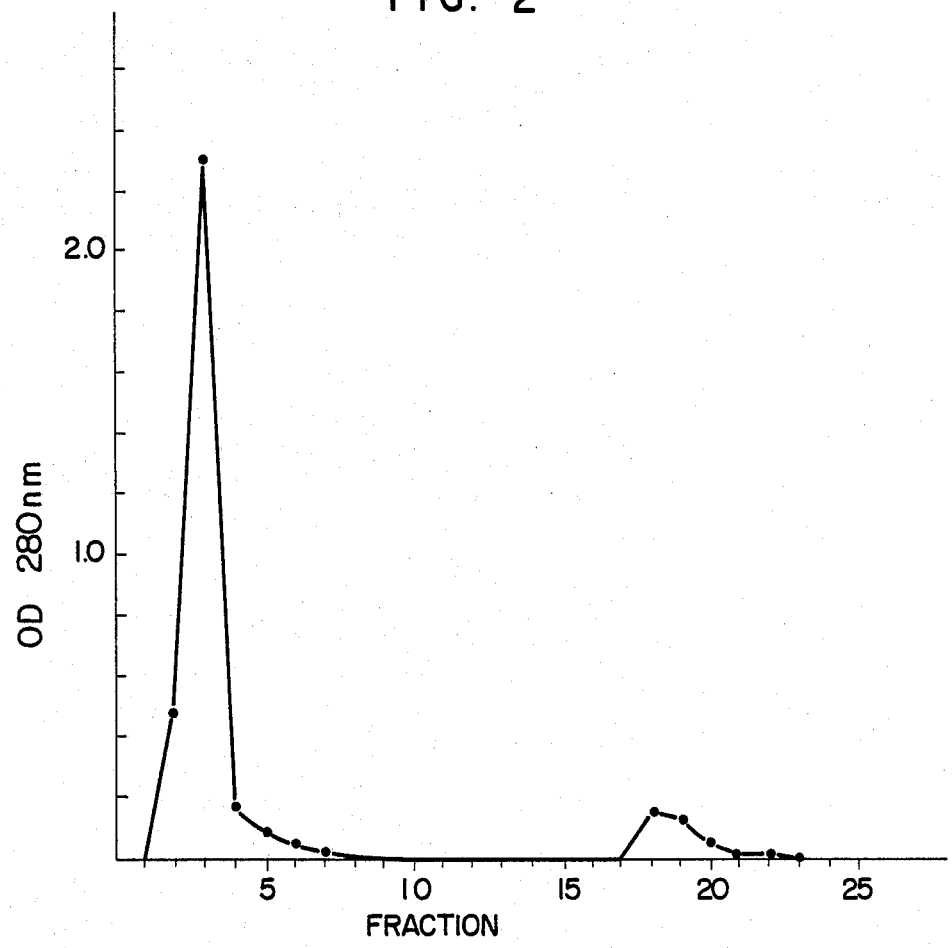

The resulting chromatogram was as shown in FIG. 2. The fraction corresponding to the first peak of the chromatogram was recovered as purified anti-AML monoclonal antibody Lot TN 008P. Table 1 shows the found cytotoxicity and specific activity values of the above precipitates and of the purified antibody.

TABLE 1

| Purification stage | Results of purification of anti-AML momoclonal antibody Lot TN 008 | | | |
|---|---|---|---|---|
| | $OD_{280}$ nm | Volume | Cytotoxicity value | Specific activity |
| 1. Ascites | 15.0 | 100 | $1 \times 10^6$ | 1:66,666 |
| 2. First fractional precipitation with $(NH_4)_2SO_4$ | | | | |
| Precipitate | 1.8 | 310 | $3.3 \times 10^5$ | 1:183,333 |
| Supernatant | 1.6 | 480 | — | — |
| 3. Second fractional precipitation with $(NH_4)_2SO_4$ | | | | |
| Precipitate | 8.2 | 50 | $2 \times 10^6$ | 1:243,902 |
| Supernatant | 0.065 | 440 | — | — |
| 4. DEAE-Cellulofine column chromatography | | | | |
| First peak fraction | 2.20 | 80 | $1.5 \times 10^6$ | 1:681,818 |
| Remainder fraction | 0.168 | 160 | $6 \times 10^4$ | — |

The activated Sepharose 4B (200 ml) was reacted with the first peak fraction (50 ml) of the DEAE-Cellulofine column chromatography with stirring at 4° C. for 16 hours, giving insolubilized anti-AML monoclonal antibody Lot TN 008P combining with Sepharose 4B. This antibody (about 1 ml) is aseptically placed in a filter-incubator as shown in FIG. 1. That is, the antibody was sterilized with ethylene oxide and placed in the filter-incubator which had been autoclave-sterilized.

The AML-cell eliminating effect of the filter-incubator thus arranged was examined in the following manner. Bone marrow of an AML patient in a remission stage was taken out. Established AML cell line GC-50 ($10^3$ cells/ml) was added to the bone marrow ($10^6$ cells/ml), and 3 ml of the mixture was placed in the arranged filter-incubator and incubated at 37° C. for 60 minutes while rotating it. Then, the filter-incubator is cooled to room temperature, 3.0 ml of the patient serum complement was added, and the incubation was further continued for 2 hours while rotating also. Table 2 shows results of this test for AML-cell eliminating effect and values of CFU-C, CFU-E, BFU-E, and CFU-TL on the bone marrow before and after the above treatment.

TABLE 2

| Item | Before treatment | After treatment |
|---|---|---|
| Method using established tumor cell lines as indicator (established cell line: GC-50) | AML cells and HL-60 were observed morphologically and genetically | Neither AML cells nor HL-60 was observed morphologically or genetically |
| Fluorescence activated cell sorter analysis | AML cells 1.02 × 10⁴/ml | no AML cell was detected |
| CFU-C | 113 | 125 |
| CFU-E | 226 | 243 |
| BFU-E | 44 | 38 |
| CFU-TL | 282 | 275 |

As indicated above, the filter-incubator provided with the insolubilized anti-AML monoclonal antibody eliminates or destroys AML cells and the treated bone marrow is nontoxic to normal hematopoietic stem cells.

The cytotoxicity of anti-AML monoclonal antibody Lot TN 008 to normal cells and to leukemia cells were as shown in Table 3. Results of tests for the cytotoxicity thereof to human established cell lines are summarized in Table 4.

TABLE 3

Cytotoxicity of anti-AML monoclonal antibody Lot TN008 ascites to normal cells and to leukemia cells

| Normal cells and leukemia cells | Number of positive cells/ Number of cells tested (Titer) |
|---|---|
| AML | 48/53 (1:10⁶) |
| CML | 0/20 |
| ALL | 0/32 |
| CLL | 0/14 |
| T-PBL | 0/42 |
| PHA-Stimulated PBL | 0/13 |
| B-PBL | 0/19 |
| BM | 0/8 |
| Monocyte | 0/31 |
| Granulocytes | 0/37 |
| T cell | 0/66 |
| B cell | 0/54 |

TABLE 4

Cytotoxicity of anti-AML monclonal antibody Lot TN008 (ascites) to human established cell lines

| Human established cell lines | Cytotoxicity value |
|---|---|
| HG (AML) | 1:10⁶ |
| GC-50 (AML) | 1:10⁶ |
| G-721 (CML) | not reacted |
| G-9308 (TALL) | " |
| NTF-5 (TALL) | " |
| Nai (null ALL) | " |
| Hana (Burkitt's Lymphoma) | " |
| IV-10 (B Lymphoblasts) | " |

In these tests, the normal cells were sampled from the peripheral blood of normal volunteers, the normal peripheral lymphocytes were separated therefrom by using Ficoll-Hypaque, T-and B-lymphocytes were separated by the E-Rosette method and the nylon wool method. The monocytes and the granulocytes were separated by the method of Cicciarelli et al. [Transplant. Proc., 10, 863 (1978)] and the method of El-Awor et al. [Tissue Antigens, 15, 346 (1980)], respectively, purities of which were ascertained by measuring the cell sizes with a coulter counter. The leukemia cells were sampled from ALL, AML, CLL, CML, and TALL patients, isolated, and stored in liquid nitrogen, in the same manner as in the case of AML cells.

The culture cell groups used were established cell line groups of HG, GC-50 (AML), G 721 (CML), G-9308, NTF-5 (TALL), Nai (null ALL), Hana (Burkitt's lymphoma), and IV-10 (B lymphoblasts). These groups of cells were proliferated in RPMI media containing 10% bovine fetal serum, at 37° C. in an atmosphere of 5% $CO_2$ in air.

The micro cytotoxicity tests were conducted in accordance with the method of Terasaki et al., ["Microdroplet Testing for HLA-A,-B,-C, and-D Antigens", Am. J. Clin. Pathol., 69, 103 (1978)].

What is claimed is:

1. A device for eliminating, or destroying and removing, tumor cells from bone marrow or from blood, the resulting bone marrow or resulting blood being administered into the human body, which device comprises:
    an inlet for introducing the bone marrow or blood containing tumor cells;
    an outlet for withdrawing the resulting bone marrow or resulting blood;
    a chamber containing a bed of carrier-bound particulate water-insoluble antitumor monoclonal antibody between the inlet and outlet;
    filter means between said bed and said outlet and said inlet, respectively, to prevent the outflow of said monoclonal antibody from said chamber, the filter means having filter pores which are smaller than $40\mu$ in diameter and the monoclonal antibody particles having a particle size greater than $40\mu$ in diameter;
    means for agitating the bed while it is in contact with bone marrow or blood fed into the chamber; and
    means for aseptically incubating the mixture of the bed and bone marrow or blood in said chamber.

2. A device according to claim 1, wherein the particulate water-insoluble antitumor monoclonal antibody has a particle diameter of $40$–$190\mu$.

3. A device according to claim 1, wherein the monoclonal antibody is an anti-acute myeloid lekemia (AML) monoclonal antibody.

4. A device according to claim 1, wherein the monoclonal antibody is reactive with HG (AML), GC-50 (AML) or HL-60 cells.

5. A device according to claim 1 which is for the treatment of bone marrow.

* * * * *